United States Patent
Valdez et al.

(10) Patent No.: US 10,189,864 B2
(45) Date of Patent: Jan. 29, 2019

(54) METAL COMPLEXES BASED ON A BIS(2-PYRIDYLMETHYL)AMINE-BASED SCAFFOLD AND METHODS OF MAKING THE SAME

(71) Applicant: Lawrence Livermore National Security, LLC, Livermore, CA (US)

(72) Inventors: Carlos Valdez, San Ramon, CA (US); Edmond Y. Lau, Dublin, CA (US); Brian P. Mayer, San Francisco, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 15/048,921

(22) Filed: Feb. 19, 2016

(65) Prior Publication Data

US 2017/0240569 A1 Aug. 24, 2017

(51) Int. Cl.

| | | |
|---|---|---|
| *C07F 1/08* | (2006.01) | |
| *C07D 401/14* | (2006.01) | |
| *C07F 3/06* | (2006.01) | |
| *C07F 15/02* | (2006.01) | |
| *C07F 15/04* | (2006.01) | |
| *C07F 15/06* | (2006.01) | |
| *A62D 3/38* | (2007.01) | |
| *A62D 101/26* | (2007.01) | |
| *A62D 101/02* | (2007.01) | |
| *A62D 101/04* | (2007.01) | |
| *A62D 101/45* | (2007.01) | |

(52) U.S. Cl.
CPC .................. *C07F 1/08* (2013.01); *A62D 3/38* (2013.01); *C07D 401/14* (2013.01); *C07F 3/06* (2013.01); *C07F 15/025* (2013.01); *C07F 15/045* (2013.01); *C07F 15/065* (2013.01); *A62D 2101/02* (2013.01); *A62D 2101/04* (2013.01); *A62D 2101/26* (2013.01); *A62D 2101/45* (2013.01)

(58) Field of Classification Search
None
See application file for complete search history.

(56) References Cited

U.S. PATENT DOCUMENTS

| | | |
|---|---|---|
| 5,663,333 A | 9/1997 | Hodge et al. |
| 6,274,051 B1 | 8/2001 | Cronce |
| 6,472,386 B1 | 10/2002 | Kodama et al. |
| 7,091,196 B2 | 8/2006 | Wang et al. |
| 2017/0253568 A1 | 9/2017 | Valdez et al. |

FOREIGN PATENT DOCUMENTS

WO    2009095394 A1    8/2009

OTHER PUBLICATIONS

Benoist et al. Carbohydrate Research, 346, 2011, 26-34.*
Yao et al. Tetrahedron Letters, 57, 2016, 910-913.*
You et al. (Inorganica Chimica Acta, 423, 2014, 332-339.*
Organic Letters, 9(24), 4999-5002 (Year: 2007).*
Restriction Requirement from U.S. Appl. No. 15/059,232, dated Nov. 4, 2016.
Valdez et al., U.S. Appl. No. 15/059,232, filed Mar. 2, 2016.
Non-Final Office Action from U.S. Appl. No. 15/059,232, dated Aug. 30, 2017.
Guo et al., "Coordination chemistry of heterocycle-functionalized diazamesocycles: tuning the productive NiII complexes through altering the pendants of ligands," Inorganics Chimica Acta, vol. 358, 2005, pp. 1887-1896.
Du et al., "Synthesis, crystal structure and properties of the CuII complex of a tetradentate imidazole-functionalized diazamesocyclic ligand, 1,4-bis(N-1-methylimidazol-2-yl-methyl)-1,4-diazacycloheptane," Journal of Molecular Structure, vol. 641, 2002, pp. 29-34.
Playa et al., Dilazep analogues for the study of equilibrative nucleoside transporters 1 and 2 (ENT1 and ENT2), Bioorganic & Medicinal Chemistry Letters, vol. 24, 2014, pp. 5801-5804.
Final Office Action from U.S. Appl. No. 15/059,232, dated Apr. 16, 2018.
Notice of Allowance from U.S. Appl. No. 15/059,232, dated Jun. 20, 2018.

* cited by examiner

*Primary Examiner* — Yun Qian
(74) *Attorney, Agent, or Firm* — Zilka-Kotab

(57) ABSTRACT

A catalyst includes a bis(2-pyridylmethyl)amine-based ligand. A method of forming a catalyst, may include: reacting bis(2-pyridylmethyl)amine-based compound with a terminal azide and/or a terminal alkyne in the presence of Cu(I) to form a bis(2-pyridylmethyl)amine-based ligand. A method of using such catalysts may include neutralizing toxicity of at least one organophosphorus-based compound by reacting the organophosphorus-based compound with a bis(2-pyridylmethyl)amine-based ligand-metal complex.

14 Claims, 10 Drawing Sheets

METAL COMPLEXES BASED ON A BIS(2-PYRIDYLMETHYL)AMINE-BASED SCAFFOLD AND METHODS OF MAKING THE SAME

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to catalysts, and more particularly, this invention relates to metal complexes based on a bis(2-pyridylmethyl)amine-based scaffold, as well as methods of making and using the same.

BACKGROUND

The use of organophosphorus-based compounds as pesticides, solvents, and plasticizers is well-known and effective in the intended capacity. However, persistence of these compounds in the environment leads to adverse collateral impact, and several known organophosphorus-based compounds are acutely toxic nerve agents to insects and humans. The adverse effects are compounded by the fact that these organophosphorus-based compounds are highly toxic even at low doses, capable of being absorbed through skin, and very fast-acting.

In particular, toxicity of organophosphorus-based compounds arises from a structural motif characterized by an electrophilic phosphorous oxide center in which the phosphorous atom is bonded to one or more, typically three, substituents, one of which is capable of acting as a leaving group. In vivo, the leaving group of the organophosphorus-based compound departs and the compound irreversibly inactivates the acetylcholinesterase (AChE) enzyme, disrupting the nervous system's ability to modulate muscular contractions. Disruption of smooth muscle tissue in the respiratory system leads to rapid death upon exposure to these toxic organophosphorus-based compounds, even at very low dosages.

Exemplary toxic organophosphorus-based compounds shown in FIGS. 1A-1E include Paraoxon (diethyl 4-nitrophenyl phosphate); VX (O-ethyl S-[2-(diisopropylamino)ethyl]methylphosphonothioate); VR (N,N-diethyl-2-(methyl-(2methylpropoxy)phosphoryl)sulfanylethanamine); Sarin gas/GB ((RS)-propan-2-yl methylphosphonofluoridate); and GF (cyclohexyl methylphosphonofluoridate). With regard to Paraoxon, the leaving group is the p-nitrophenol moiety, while for the V-series agents VX and VR, the leaving group is the 2-aminothiol moiety. Additionally, the leaving group for the G-series agents GB and GF is the fluoride ion.

Several existing techniques for inactivating or otherwise neutralizing organophosphorus-based compounds have been proposed, but generally rely on using excessive amounts of highly caustic agents such as bleach, sodium hydroxide and/or potassium hydroxide (e.g., pH≥12), which tends to damage or destroy the material to which the neutralizing agent is applied. Existing catalytic approaches rely on excessive amounts of organic solvents such as alcohols to accomplish neutralization, as well as rare and/or expensive catalysts including iridium, platinum, and/or palladium. Conventional catalytic approaches have also been troubled by a tendency for the catalyzed products to subsequently react with the catalyst, inhibiting or destroying catalytic capabilities. Particularly when using such expensive metals as catalysts, this inhibition further reduces efficiency of the overall neutralization process and exacerbates the expense of accomplishing effective neutralization. As such, the conventional techniques are expensive, and cause extensive collateral damage to the treated materials and/or the environment (e.g., where the organophosphorus-based compounds are employed as pesticides).

Accordingly, it would be of significant environmental and economic benefit to provide novel, freely available, and inexpensive materials, synthetic techniques, and deployment methods for the destruction of organophosphorus-based compounds.

SUMMARY

In one embodiment, a catalyst includes a bis(2-pyridylmethyl)amine-based ligand.

In another embodiment, a method of forming a catalyst includes: reacting bis(2-pyridylmethyl)amine-based compound with a terminal azide and/or a terminal alkyne in the presence of Cu(I) to form a bis(2-pyridylmethyl)amine-based ligand.

In still yet another embodiment, a method of using catalysts as disclosed herein includes neutralizing toxicity of at least one organophosphorus-based compound by reacting the organophosphorus-based compound with a bis(2-pyridylmethyl)amine-based ligand-metal complex.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

Figure 2D:
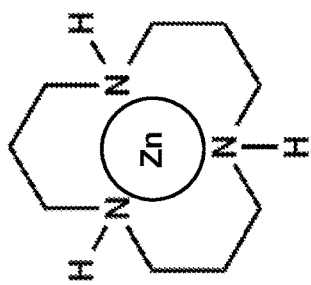
FIGS. 2A-2D depict simplified schematics of several known zinc-based catalysts that do not employ bis(2-pyridylmethyl)amine-based compounds.
Figure 2C:
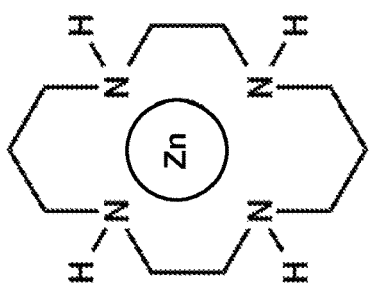
Figure 2:
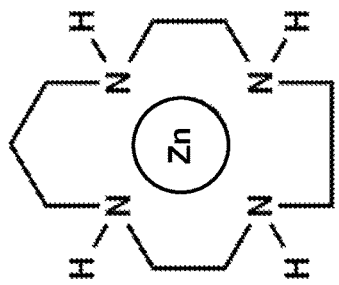
Figure 2A:
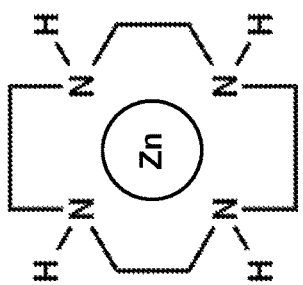

In various approaches, $Zn^{2+}$ based catalysts, particularly $Zn^{2+}$ coordinated azamacrocycles, may be useful for the degradation of various organophosphorus-based compounds, as well as for carbon capture processes (e.g., the conversion of carbon dioxide into bicarbonate). FIGS. 2A-2D illustrate four exemplary $Zn^{2+}$ coordinated azamacrocycles, each of which have the $Zn^{2+}$ metal coordinated by the nitrogen atoms in their respective ligands. In particular, FIG. 2A depicts the [12]aneN4 catalyst (also known as "1,4,7,10-tetraazacyclododecane" or "cyclen"); FIG. 2B depicts the [13]aneN4 catalyst (also known as "1,4,7,10-tetraazacyclotridecane"); FIG. 2C depicts the [14]aneN4 catalyst (also known as "1,4,8,11-tetraazacyclotetradecane"); and FIG. 2D depicts the [12]aneN3 catalyst (also known as "1,5,9-triazacyclododecane"). With respect to the ligands shown FIGS. 2A-2C, the complexation involves a total of four nitrogen atoms, whereas for the ligand shown in FIG. 2D, the complexation involves a total of three nitrogen atoms.

Each of the $Zn^{2+}$ based catalysts shown in FIGS. 2A-2D may include a water molecule as an additional ligand (a fifth ligand in the case of the $Zn^{2+}$ based catalysts of FIGS. 2A-2B, and a fourth ligand in the case of the $Zn^{2+}$ based catalyst of FIG. 2D), where the water molecule, upon complexation to the metal center, becomes more acidic than when it is in its unbound state. For such $Zn^{2+}$ based catalysts, the arrangement of nitrogen centers in conjunction with the carbon framework linking the nitrogen centers together changes the Zn—O bond distance, thereby producing electronic changes as well as lowering the pKa value of the coordinated water molecule. Accordingly, the $pK_a$ of the coordinated water molecule in such $Zn^{2+}$ based catalysts may be in a range from about 6.0-10.0, in contrast to having a value of about 15.7 (the $pK_a$ of water in its unbound state).

The $pK_a$ values of the $Zn^{2+}$ based catalysts shown in FIGS. 2A-2D are as follows: [12]aneN4, $pK_a$~8.1 (FIG. 2A); [13]aneN4, $pK_a$~8.3 (FIG. 2B); [14]aneN4, $pK_a$~9.8 (FIG. 2C); and [12]aneN3, $pK_a$~7.3 (FIG. 2D). It has been found that the [12]aneN3 catalyst of FIG. 2D exhibits higher catalytic activity than the other $Zn^{2+}$ based catalysts of FIGS. 2A-2C, where such higher catalytic activity is directly linked to the $pK_a$ value of the water molecule coordinated to the metal center. For instance, as the $pK_a$ value of the coordinated water molecule is at its lowest in the [12]aneN3 catalyst of FIG. 2D, the water molecule's conversion to a hydroxide ion is more likely at basic pH values than in the $Zn^{2+}$ based catalysts of FIGS. 2A-2C.

It is of note, however, that the synthesis of conventional $Zn^{2+}$ based catalysts, such as those shown in FIGS. 2A-2D, is cumbersome, inefficient, and costly in comparison to the synthesis of the inventive bis(2-pyridylmethyl)amine-based compounds disclosed herein.

Accordingly, embodiments disclosed herein are directed to metal complexes based on a bis(2-pyridylmethyl)amine scaffold, as well as methods of making and using the same. Advantageously, the presently disclosed methods of synthesis and implementations of metal complexes based on a bis(2-pyridylmethyl)amine scaffold rely on cost effective, highly-available materials (both regarding the catalytic metal cations and the organic ligands), as well as simple, high-yield synthetic techniques.

Additionally, the precursor and/or intermediate compounds (examples of which are depicted in FIGS. 6, 8, 10, and 12) used to form the bis(2-pyridylmethyl)amine-based ligands disclosed herein are suitable for use in generating libraries of organic ligands capable of chelating a metal cation. In particular, multiple nitrogen atoms of bis(2-pyridylmethyl)amine-based ligands have been discovered to strongly bind metal cations, allowing subsequent formation of a complex between the chelated metal cation and a water molecule. Advantageously, these bis(2-pyridylmethyl) amine-based compounds chelate the metal cation with sufficient strength to prevent subsequent inhibition of the catalytic activity, e.g. due to reaction or complexation with products of the catalysis. Moreover, the bis(2-pyridylmethyl)amine-based ligands disclosed herein are preferably characterized by a high degree of structural integrity and rigidity, such that the compounds may retain their structure even when subjected to temperatures sufficient to boil water (100 C).

Further, the formation and use of the bis(2-pyridylmethyl) amine-based ligand-metal complexes disclosed herein confers significant economic advantage with regard to neutralizing toxicity of organophosphorus-based compounds and carbon capture processes as compared to conventional approaches, such as those utilizing the $Zn^{2+}$ based catalysts shown in FIGS. 2A-2D. Moreover, the presently disclosed bis(2-pyridylmethyl)amine-based ligand-metal complexes and implementations thereof accomplish neutralization of toxic organophosphorus-based compounds without relying on caustic agents such as bleach, high-pH materials such as sodium or potassium hydroxide solutions; or organic solvents such as alcohols. Rather, in particular approaches, the presently disclosed bis(2-pyridylmethyl)amine-based ligand-metal complexes may carry out neutralization using only water as an intermediary, e.g. to provide a hydroxyl moiety to substitute for a leaving group of the organophosphorus-based compound, and optionally to carry away cleaved leaving group moieties and/or neutralized organophosphorus-based compounds from a substrate being treated. The presently disclosed inventive concepts are thus characterized by facile deployment using a variety of environmentally friendly solvents, buffer, materials, etc. to facilitate neutralization.

Following are several examples of general and specific embodiments of metal complexes based on a bis(2-pyridylmethyl)amine scaffold, and/or methods of making and using the same.

For instance, in one general embodiment, a catalyst includes a bis(2-pyridylmethyl)amine-based ligand.

In another general embodiment, a method of forming a catalyst includes: reacting bis(2-pyridylmethyl)amine-based compound with a terminal azide and/or a terminal alkyne in the presence of Cu(I) to form a bis(2-pyridylmethyl)amine-based ligand.

In still yet another general embodiment, a method of using catalysts as disclosed herein includes neutralizing toxicity of at least one organophosphorus-based compound by reacting the organophosphorus-based compound with a bis(2-pyridylmethyl)amine-based ligand-metal complex.

In one preferred embodiment, the novel catalysts disclosed herein may include a ligand coordinated/complexed to a metal cation ($M^{2+}/M^{3+}$). In some approaches, the metal cation may include $Zn^{2+}$, $Co^{2+}$, $Cu^{2+}$, $Ni^{3+}$, $Fe^{3+}$, or other such suitable metal cation as would become apparent to one having ordinary skill in the art upon reading the present disclosure.

In more approaches, the ligand may include at least four nitrogen atoms configured to coordinate the metal cation. In yet more approaches, the ligand may include at least three $sp^2$ nitrogen atoms, and at least one $sp^3$ nitrogen atom, each of which are configured to coordinate the metal cation. In further approaches, the novel catalysts disclosed herein may include water or a hydroxyl moiety coordinated/complexed to the metal cation.

Figure 3:
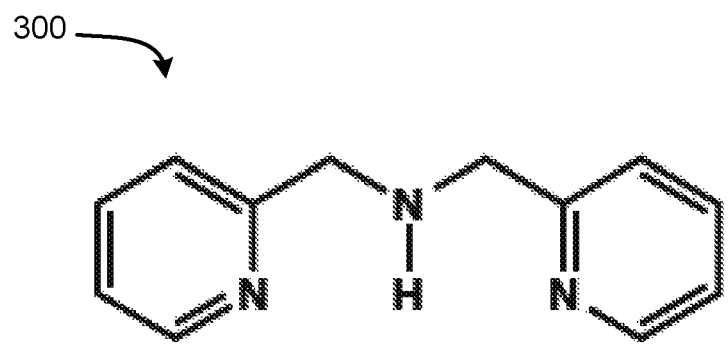
FIG. 3 depicts a simplified schematic of bis(2-pyridylmethyl)amine.

In preferred approaches, the ligand may be synthesized using the starting material bis(2-pyridylmethyl)amine 300 as shown in FIG. 3. Bis(2-pyridylmethyl)amine 300 (also referred to as dipicolyamine) is inexpensive and can be purchased in multi-gram quantities, making the production of a compound library an economically efficient task. Of course, skilled artisans in the field of synthetic organic chemistry will appreciate that bis(2-pyridylmethyl)amine 300 shown in FIG. 3 is merely an exemplary starting material, and should not be considered limiting on the scope of the presently disclosed inventive concepts. Equivalent pyridine-based starting materials are also to be considered within the scope of the present invention, as would be understood by a person having ordinary skill in the art upon reading the present disclosure.

In additional approaches, the presently disclosed inventive bis(2-pyridylmethyl)amine-based ligands, catalytic complexes, and equivalents thereof may be employed using a variety of solvents, buffers, etc. and preferably environmentally friendly solvents, buffers, etc. as would become apparent to a person having ordinary skill in the art upon reading the present disclosure. For example, according to one particular approach, a suitable solvent may be water, but may also include organic phase solvents, peroxides, salts, etc. The solvent may preferably have a pH in a range from about 7.0 to about 7.4 to facilitate substitution mediated by the novel catalysts (e.g., the bis(2-pyridylmethyl)amine-based ligand-metal complexes) disclosed herein. In addition, the active catalyst may preferably be loaded in the buffer, solvent, etc. in a particular molar ratio with respect to the amount of an agent to be neutralized (e.g., an organophosphorus-based compound). In preferred approaches, the decontamination solution preferably is loaded with the novel catalysts disclosed herein in an amount ranging from about 10 mol % to about 50 mol % with respect to the organophosphorus-based compound to be neutralized.

Figure 4:
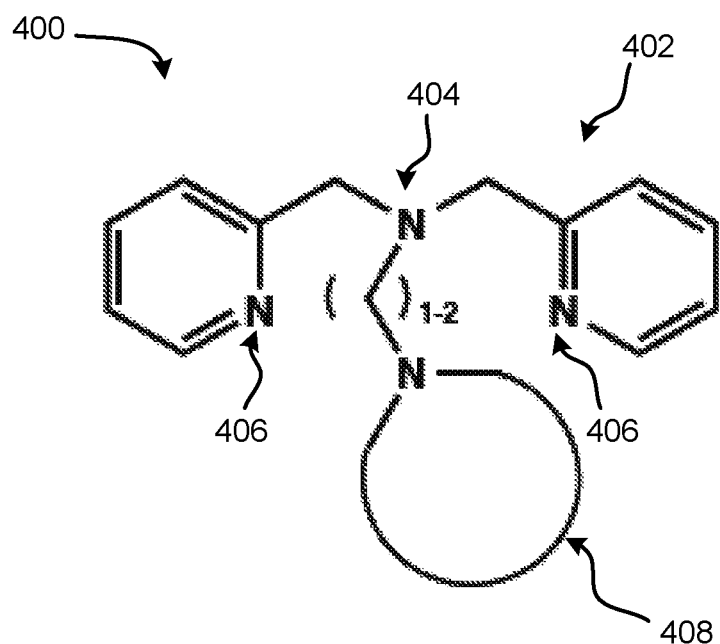
FIG. 4 depicts a simplified schematic of a bis(2-pyridylmethyl)amine ligand suitable for use in the novel catalysts disclosed herein, according to one embodiment.

Referring now to FIG. 4, the general structure of a bis(2-pyridylmethyl)amine ligand 400 suitable for use in the novel catalysts disclosed herein is shown according to one embodiment. As an option, the bis(2-pyridylmethyl)amine ligand 400 may be implemented in conjunction with features from any other embodiment listed herein, such as those described with reference to the other FIGS. Of course, the bis(2-pyridylmethyl)amine ligand 400 and others presented herein may be used in various applications and/or in permutations which may or may not be specifically described in the illustrative embodiments listed herein. Further, the bis (2-pyridylmethyl)amine ligand 400 presented herein may be used in any desired environment.

As shown in FIG. 4, the bis(2-pyridylmethyl)amine ligand 400 may include at least a bis(2-pyridylmethyl)amine scaffold 402. This bis(2-pyridylmethyl)amine scaffold 402 includes three nitrogen atoms (e.g., one central $sp^3$ nitrogen atom 404, and two $sp^2$ nitrogen atoms 406 from the pyridine rings) configured to coordinate a metal cation (not shown). In preferred approaches, the bis(2-pyridylmethyl)amine ligand 400 may additionally comprise a heterocyclic moiety 408 coupled to the bis(2-pyridylmethyl)amine scaffold 402. This heterocyclic moiety 408 may include at least one nitrogen atom, thereby yielding a tetradentate ligand configured to coordinate a metal cation (not shown). Preferably, the heterocyclic moiety 408 may be an aromatic heterocycle including at least one $sp^2$ nitrogen atom. Exemplary heterocyclic moieties 408 may include, but are not limited to, a triazole, an imidazole, a thiazole, an oxazole, a pyrazole, etc.

As discussed in greater detail infra, formation of the aforementioned bis(2-pyridylmethyl)amine-based tetradentate ligand may be achieved via a variety of synthetic processes, preferably a process utilizing the Cu(I)-catalyzed azide-alkyne cycloaddition reaction (CuAAC or click chemistry). Utilizing click chemistry to from such a bis(2-pyridylmethyl)amine-based tetradentate ligand involves high-yielding and easy purification steps, ultimately providing the opportunity to form a library of bis(2-pyridylmethyl)amine-based ligands comprising different chemical, reactive and/or structural properties. Moreover, complexation of such pyridylmethyl)amine-based tetradentate ligands (e.g., ligand 400 of FIG. 4) to different metal cations opens their application to the areas of organophosphorus-based compound destruction, carbon capture technologies, and Structure-Activity Relationship (SAR) studies.

Figure 5:
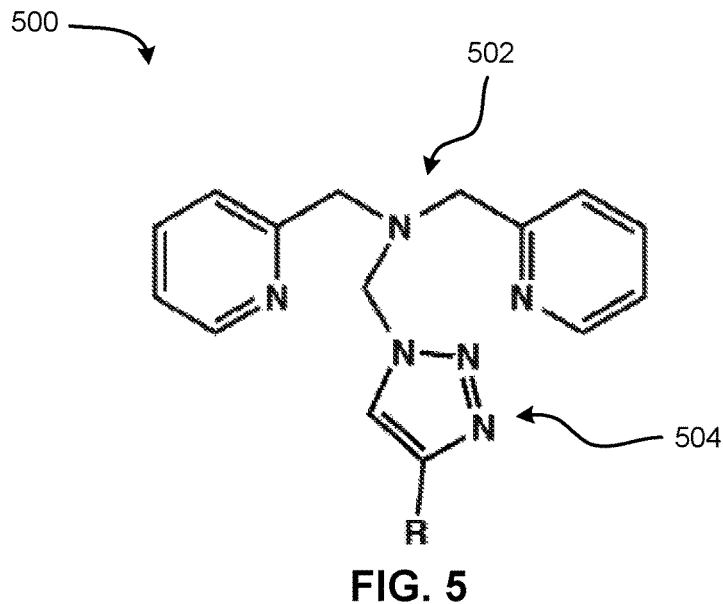
FIG. 5 depicts a simplified schematic of a first bis(2-pyridylmethyl)amine-based ligand, according to one embodiment.

Referring now to FIG. 5, a first bis(2-pyridylmethyl) amine-based ligand 500 is shown, according to one embodiment. As an option, the bis(2-pyridylmethyl)amine-based ligand 500 may be implemented in conjunction with features from any other embodiment listed herein, such as those described with reference to the other FIGS. Of course, the bis(2-pyridylmethyl)amine-based ligand 500 and others presented herein may be used in various applications and/or in permutations which may or may not be specifically described in the illustrative embodiments listed herein. Further, the bis(2-pyridylmethyl)amine-based ligand 500 presented herein may be used in any desired environment.

As shown in FIG. 5, the bis(2-pyridylmethyl)amine-based ligand 500 includes a bis(2-pyridylmethyl)amine scaffold 502 and a triazole moiety 504 coupled thereto. The R group associated with the triazole moiety 504 may be selected based on the manner in which the bis(2-pyridylmethyl) amine-based ligand 500 is to be employed, e.g. to confer additional advantageous functionality. Exemplary R groups may include, but are not limited to: one or more electron donating groups, e.g., to facilitate binding of the metal cation (not shown in FIG. 5); one or more electron withdrawing groups, e.g., to modulate the length of the Zn—$OH_2$ bond (by shortening or lengthening it) and thus directly affect the $pK_a$ of an attached water molecule (not shown) that may result in an increase nucleophilicity and activity of the complex; one or more solubilizing ligands such as an alcohol or polyethylene glycol (PEG), e.g., to tune solubility of the bis(2-pyridylmethyl)amine-based ligand 500 to be compatible with a suitable solvent, buffer composition, etc.

An exemplary method 600 for forming the bis(2-pyridylmethyl)amine-based ligand 500 of FIG. 5 is shown, according to one embodiment. As an option, the present method 600 may be implemented in conjunction with features from any other embodiment listed herein, such as those described with reference to the other FIGS. Of course, the method 600 and others presented herein may be used in various applications and/or in permutations, which may or may not be specifically described in the illustrative embodiments listed herein. Moreover, more or less operations than those shown in FIG. 6 may be included in method 600, according to various embodiments.

Figure 6:
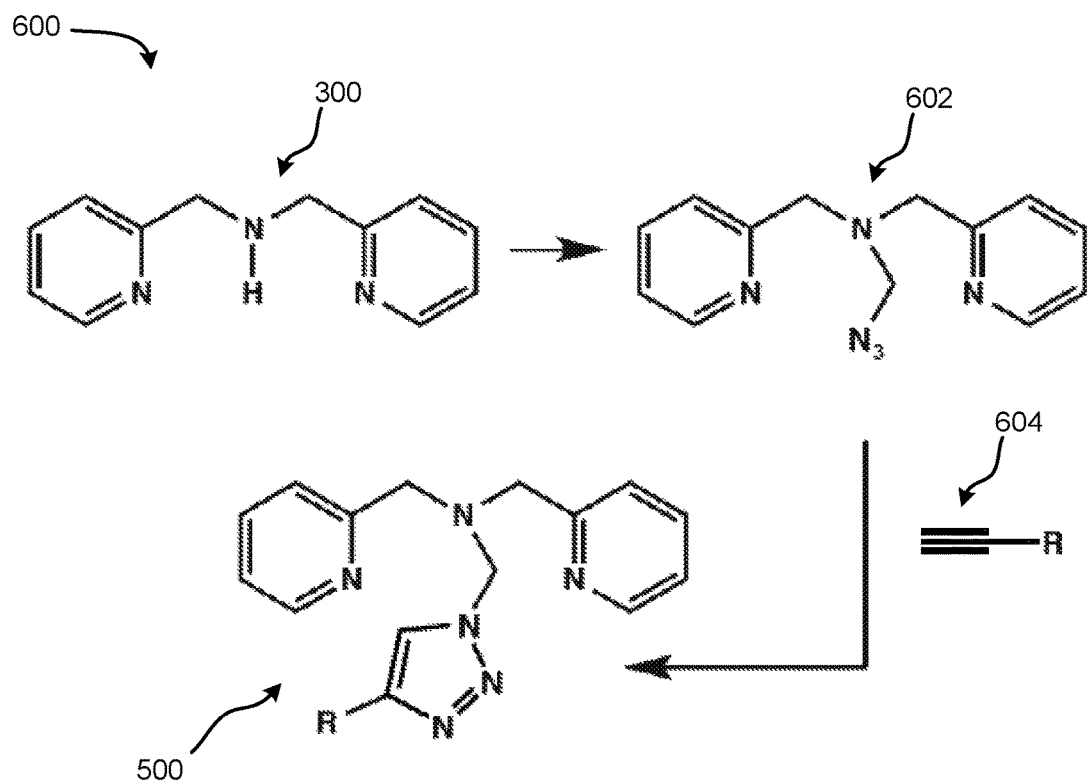
FIG. 6 depicts a simplified reaction scheme for synthesizing the first bis(2-pyridylmethyl)amine-based ligand of FIG. 5, according to one embodiment.

As shown in FIG. 6, the method 600 involves the alkoxylation of bis(2-pyridylmethyl)amine 300 (FIG. 3) using formaldehyde/methanol, followed by treatment with trimethylsilyl azide (TMSN3) to produce intermediate 602. Advantageously, the method 600 further includes reacting the intermediate 602 with an alkyne 604, preferably using click chemistry, to produce the bis(2-pyridylmethyl)amine-based ligand 500 of FIG. 5.

Advantageously, the initial step to provide the intermediate 602 utilizes inexpensive materials and high-yield synthesis, contributing to the economic efficiency of the presently disclosed inventive concepts. Moreover, this intermediate 602 may serve as the raw material suitable to produce a library of ligands having the general structure of the bis(2-pyridylmethyl)amine-based ligand 500 of FIG. 5. For instance, in various approaches, the intermediate 602 may be reacted to a panel of alkynes 604 (e.g., having different R groups from one another) to produce such a library of bis(2-pyridylmethyl)amine-based ligands.

Figure 7:
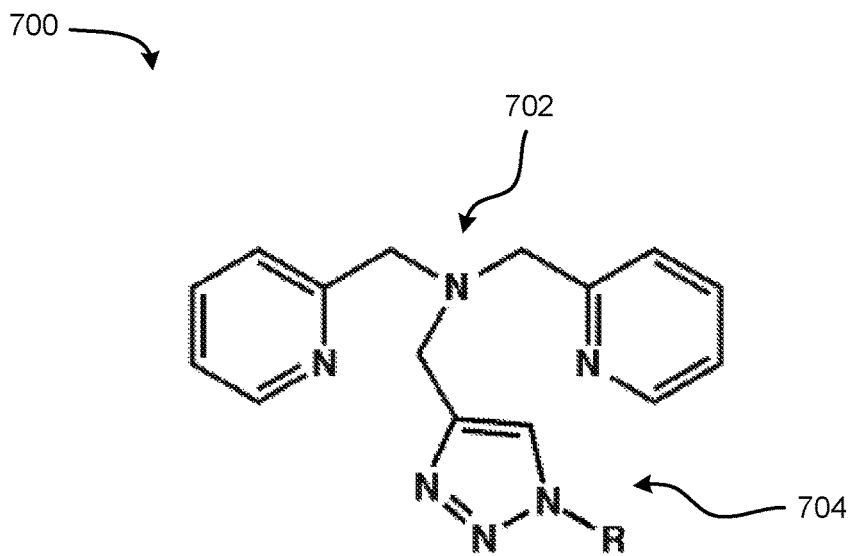
FIG. 7, depicts a simplified schematic of a second bis(2-pyridylmethyl)amine-based ligand, according to one embodiment.

Referring now to FIG. 7, a second bis(2-pyridylmethyl) amine-based ligand 700 is shown, according to another embodiment. As an option, the bis(2-pyridylmethyl)amine-based ligand 700 may be implemented in conjunction with features from any other embodiment listed herein, such as those described with reference to the other FIGS. Of course, the bis(2-pyridylmethyl)amine-based ligand 700 and others presented herein may be used in various applications and/or in permutations which may or may not be specifically described in the illustrative embodiments listed herein. Further, the bis(2-pyridylmethyl)amine-based ligand 700 presented herein may be used in any desired environment.

As shown in FIG. 7, the bis(2-pyridylmethyl)amine-based ligand 700 includes a bis(2-pyridylmethyl)amine scaffold 702 and a triazole moiety 704 coupled thereto. The R group associated with the triazole moiety 704 may be selected based on the manner in which the bis(2-pyridylmethyl) amine-based ligand 700 is to be employed, e.g. to confer additional advantageous functionality. For instance, in some approaches, the R group may include one or more electron donating groups, one or more electron withdrawing groups, one or more solubilizing ligands, or other such suitable functional group(s) as would become apparent to a person having ordinary skill in the art upon reading the present disclosure.

An exemplary method 800 for forming the bis(2-pyridylmethyl)amine-based ligand 700 of FIG. 7 is shown, according to one embodiment. As an option, the present method 800 may be implemented in conjunction with features from any other embodiment listed herein, such as those described with reference to the other FIGS. Of course, the method 800 and others presented herein may be used in various applications and/or in permutations, which may or may not be specifically described in the illustrative embodiments listed herein. Moreover, more or less operations than those shown in FIG. 8 may be included in method 800, according to various embodiments.

Figure 8:
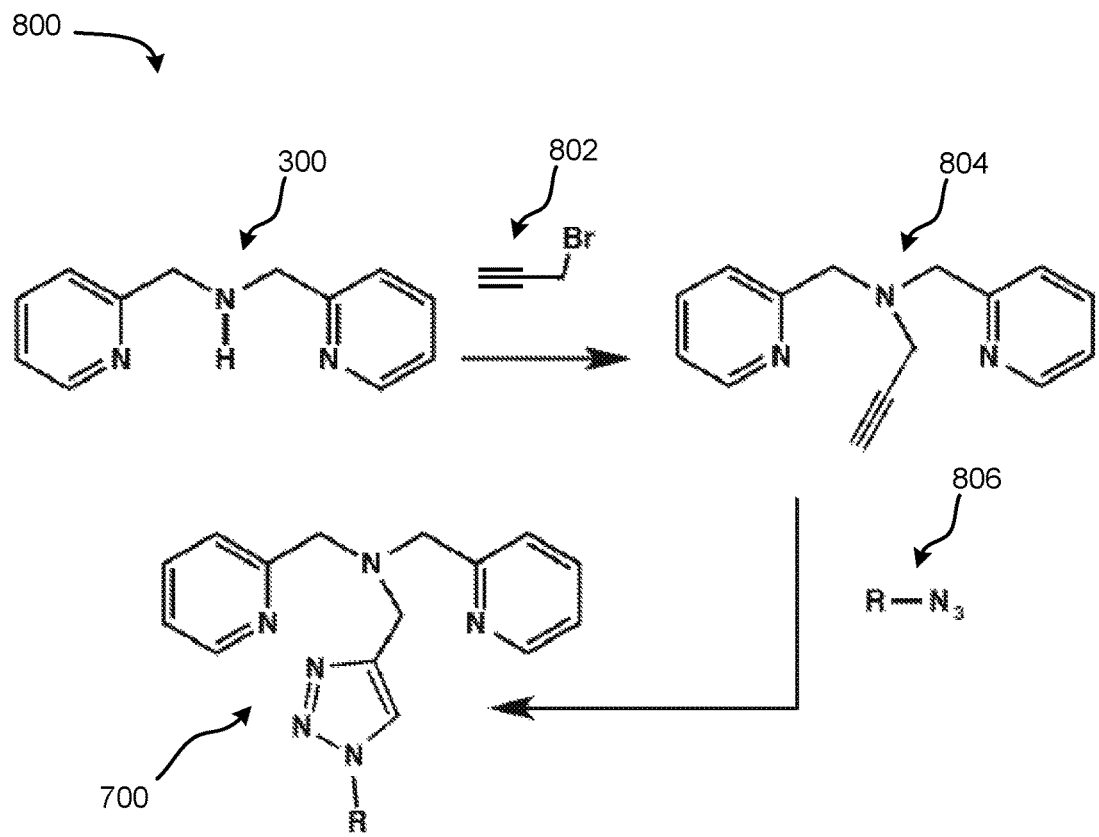
FIG. 8 depicts a simplified reaction scheme for synthesizing the second bis(2-pyridylmethyl)amine-based ligand of FIG. 7, according to one embodiment.

As shown in FIG. 8, the method 800 involves the alkylation of bis(2-pyridylmethyl)amine 300 (FIG. 3) with propargyl bromide 802 to give an alkyne intermediate 804. The alkyne intermediate 804 may subsequently be reacted with an azide 806, preferably using click chemistry, to produce the bis(2-pyridylmethyl)amine-based ligand 700 of FIG. 7.

It is of note that the alkyne intermediate 804, formed utilizing inexpensive materials and high-yield synthesis, may serve as the raw material suitable to produce a library of ligands having the general structure of the bis(2-pyridylmethyl)amine-based ligand 700 of FIG. 7. For instance, in various approaches, the intermediate 804 may be reacted to a panel of azides 806 (e.g., having different R groups from one another) to produce such a library of bis(2-pyridylmethyl)amine-based ligands.

Figure 9:
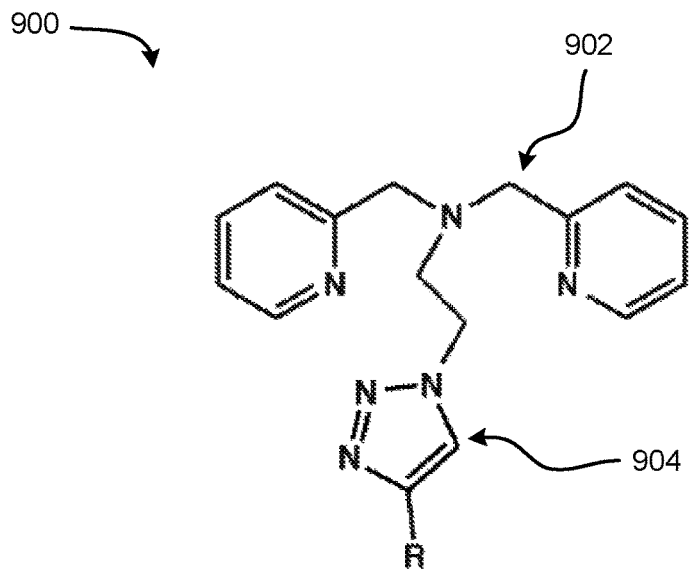
FIG. 9 depicts a simplified schematic of a third bis(2-pyridylmethyl)amine-based ligand, according to one embodiment.

Referring now to FIG. 9, a third bis(2-pyridylmethyl) amine-based ligand 900 is shown, according to another embodiment. As an option, the bis(2-pyridylmethyl)amine-based ligand 900 may be implemented in conjunction with features from any other embodiment listed herein, such as those described with reference to the other FIGS. Of course, the bis(2-pyridylmethyl)amine-based ligand 900 and others presented herein may be used in various applications and/or in permutations which may or may not be specifically described in the illustrative embodiments listed herein. Further, the bis(2-pyridylmethyl)amine-based ligand 900 presented herein may be used in any desired environment.

As shown in FIG. 9, the bis(2-pyridylmethyl)amine-based ligand 900 includes a bis(2-pyridylmethyl)amine scaffold 902 and a triazole moiety 904 coupled thereto. The R group associated with the triazole moiety 904 may be selected based on the manner in which the bis(2-pyridylmethyl) amine-based ligand 900 is to be employed, e.g. to confer additional advantageous functionality. For instance, in some approaches, the R group may include one or more electron donating groups, one or more electron withdrawing groups, one or more solubilizing ligands, or other such suitable functional group(s) as would become apparent to a person having ordinary skill in the art upon reading the present disclosure.

An exemplary method 1000 for forming the bis(2-pyridylmethyl)amine-based ligand 900 of FIG. 9 is shown, according to one embodiment. As an option, the present method 1000 may be implemented in conjunction with features from any other embodiment listed herein, such as those described with reference to the other FIGS. Of course, the method 1000 and others presented herein may be used in various applications and/or in permutations, which may or may not be specifically described in the illustrative embodiments listed herein. Moreover, more or less operations than those shown in FIG. 10 may be included in method 1000, according to various embodiments.

Figure 10:
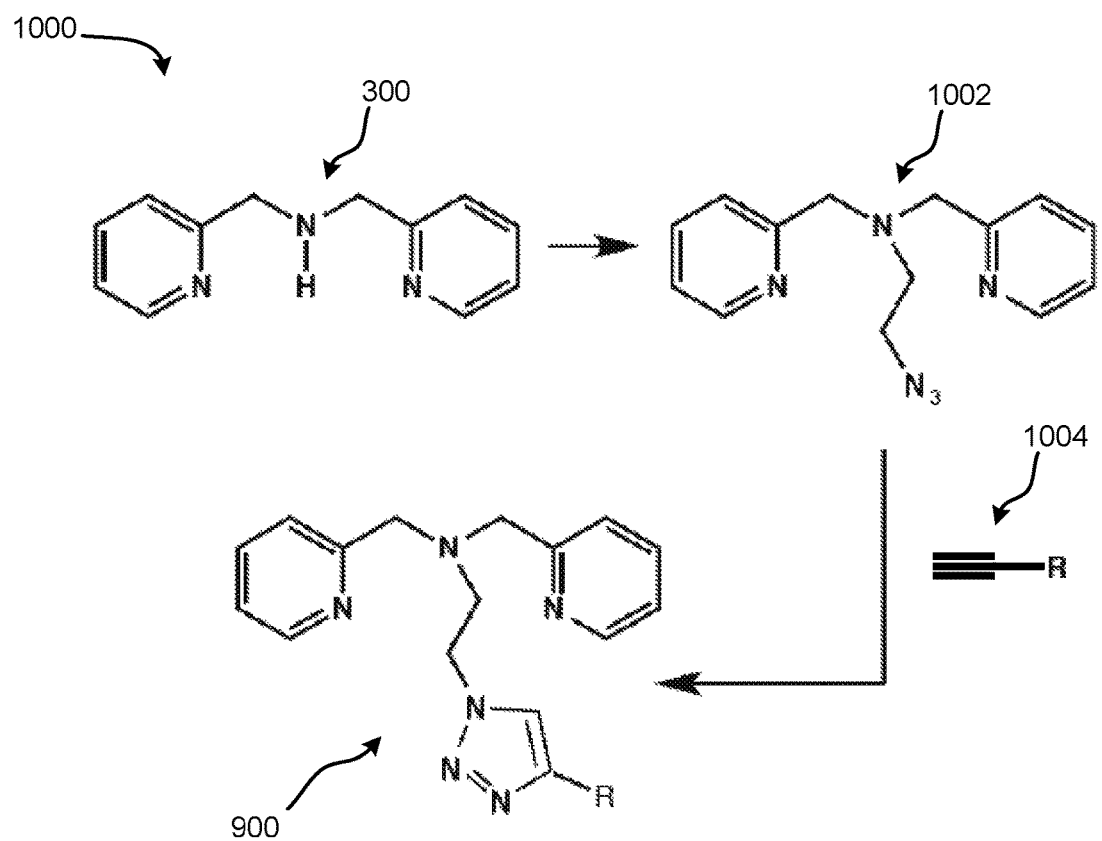
FIG. 10 depicts a simplified reaction scheme for synthesizing the third bis(2-pyridylmethyl)amine-based ligand of FIG. 9, according to one embodiment

As shown in FIG. 10, the method 1000 involves the alkylation of bis(2-pyridylmethyl)amine 300 (FIG. 3) with 2-chloroethyl bromide to yield an alkyl halide intermediate (not shown) that may then be treated with sodium azide to yield intermediate 1002. The intermediate 1002 may then be reacted with an alkyne 1004, preferably using click chemistry, to produce the bis(2-pyridylmethyl)amine-based ligand 900 of FIG. 9.

It is also of note that the intermediate 1002, formed utilizing inexpensive materials and high-yield synthesis, may serve as the raw material suitable to produce a library of ligands having the general structure of the bis(2-pyridylmethyl)amine-based ligand 900 of FIG. 9. For instance, in various approaches, the intermediate 1002 may be reacted to a panel of alkynes 1004 (e.g., having different R groups from one another) to produce such a library of bis(2-pyridylmethyl)amine-based ligands.

Figure 11:
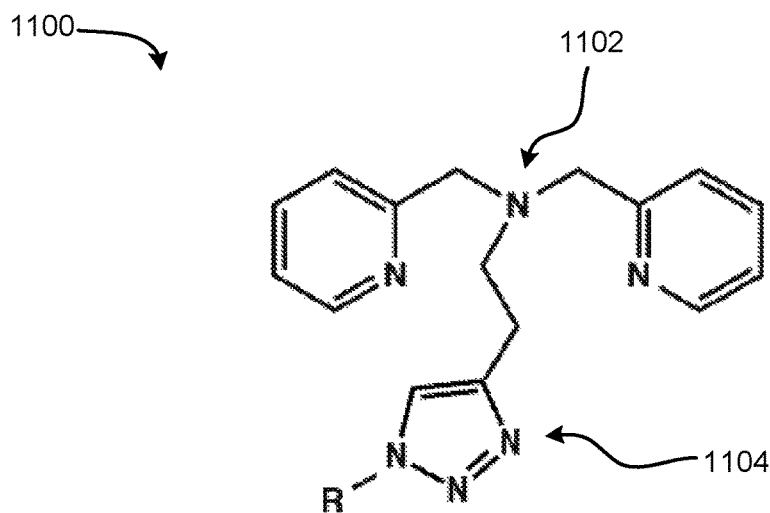
FIG. 11, depicts a simplified schematic of a fourth bis(2-pyridylmethyl)amine-based ligand, according to one embodiment.

Referring now to FIG. 11, a fourth bis(2-pyridylmethyl)amine-based ligand 1100 is shown, according to another embodiment. As an option, the bis(2-pyridylmethyl)amine-based ligand 1100 may be implemented in conjunction with features from any other embodiment listed herein, such as those described with reference to the other FIGS. Of course, the bis(2-pyridylmethyl)amine-based ligand 1100 and others presented herein may be used in various applications and/or in permutations which may or may not be specifically described in the illustrative embodiments listed herein. Further, the bis(2-pyridylmethyl)amine-based ligand 1100 presented herein may be used in any desired environment.

As shown in FIG. 11, the bis(2-pyridylmethyl)amine-based ligand 1100 includes a bis(2-pyridylmethyl)amine scaffold 1102 and a triazole moiety 1104 coupled thereto. The R group associated with the triazole moiety 1104 may be selected based on the manner in which the bis(2-pyridylmethyl)amine-based ligand 1100 is to be employed, e.g. to confer additional advantageous functionality. For instance, in some approaches, the R group may include one or more electron donating groups, one or more electron withdrawing groups, one or more solubilizing ligands, or other such suitable functional group(s) as would become apparent to a person having ordinary skill in the art upon reading the present disclosure.

An exemplary method 1200 for forming the bis(2-pyridylmethyl)amine-based ligand 1100 of FIG. 11 is shown, according to one embodiment. As an option, the present method 1200 may be implemented in conjunction with features from any other embodiment listed herein, such as those described with reference to the other FIGS. Of course, the method 1200 and others presented herein may be used in various applications and/or in permutations, which may or may not be specifically described in the illustrative embodiments listed herein. Moreover, more or less operations than those shown in FIG. 12 may be included in method 1200, according to various embodiments.

Figure 12:
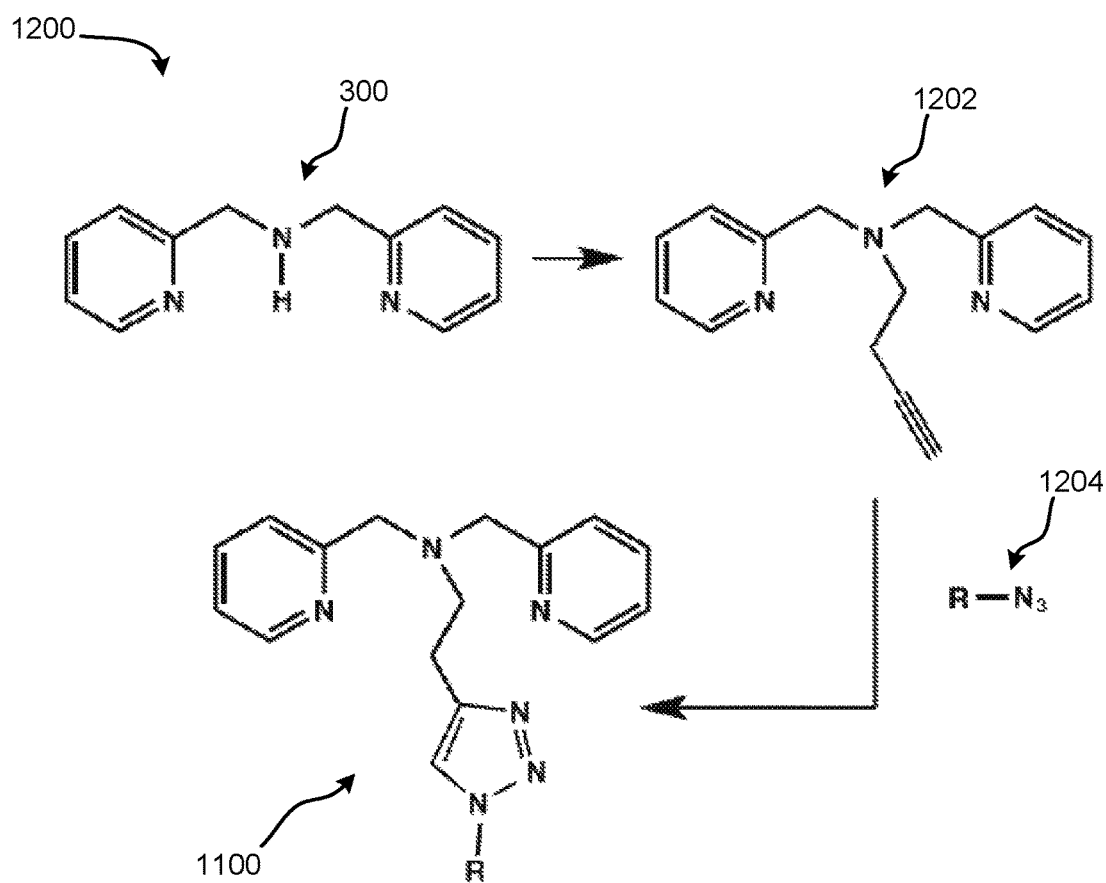
FIG. 12 depicts a simplified reaction scheme for synthesizing the fourth bis(2-pyridylmethyl)amine-based ligand of FIG. 11, according to one embodiment.

As shown in FIG. 12, the method 1200 involves the alkylation of bis(2-pyridylmethyl)amine 300 (FIG. 3) with homopropargyl bromide to yield an alkyne intermediate 1202. The alkyne intermediate 1202 may then be reacted with an azide 1204, preferably using click chemistry, to produce the bis(2-pyridylmethyl)amine-based ligand 1100 of FIG. 11.

It is again of note that the alkyne intermediate 1202, formed utilizing inexpensive materials and high-yield synthesis, may serve as the raw material suitable to produce a library of ligands having the general structure of the bis(2-pyridylmethyl)amine-based ligand 1100 of FIG. 11. For instance, in various approaches, the alkyne intermediate 1202 may be reacted to a panel of azides 1204 (e.g., having different R groups from one another) to produce such a library of bis(2-pyridylmethyl)amine-based ligands.

One of the key advantages of the synthetic schemes described in FIGS. 6, 8, 10 and 12 includes the use of a common, inexpensive starting material, namely bis(2-pyridylmethyl)amine, as well as the ultimate formation of the bis(2-pyridylmethyl)amine-based ligands in only 3-4 steps. Another key advantage to the synthetic schemes described in FIGS. 6, 8, 10 and 12 is the fact that a myriad of bis(2-pyridylmethyl)amine-based ligands having chemical, reactive and/or structural properties may be formed using the Cu(I)-catalyzed azide-alkyne cycloaddition reaction ("CuAAC" or "click chemistry"). For instance, in various approaches, the alkyne or azide used for the reaction with the intermediates (e.g., 602, 804, 1002, 1202) in the synthetic schemes shown in FIGS. 6, 8, 10 and 12 may be modified. In particular approaches, the R group of the alkyne or azide may be selected/varied to include hydrocarbon chains, esters, ethers, aromatic groups, alcohols, PEG, etc., as would become apparent to a person having ordinary skill in the art upon reading the present disclosure. In additional approaches, modifications may be made to one or more portions of the bis(2-pyridylmethyl)amine starting material, and/or one or more portions of the bis(2-pyridylmethyl)amine-based intermediate.

Figure 13:
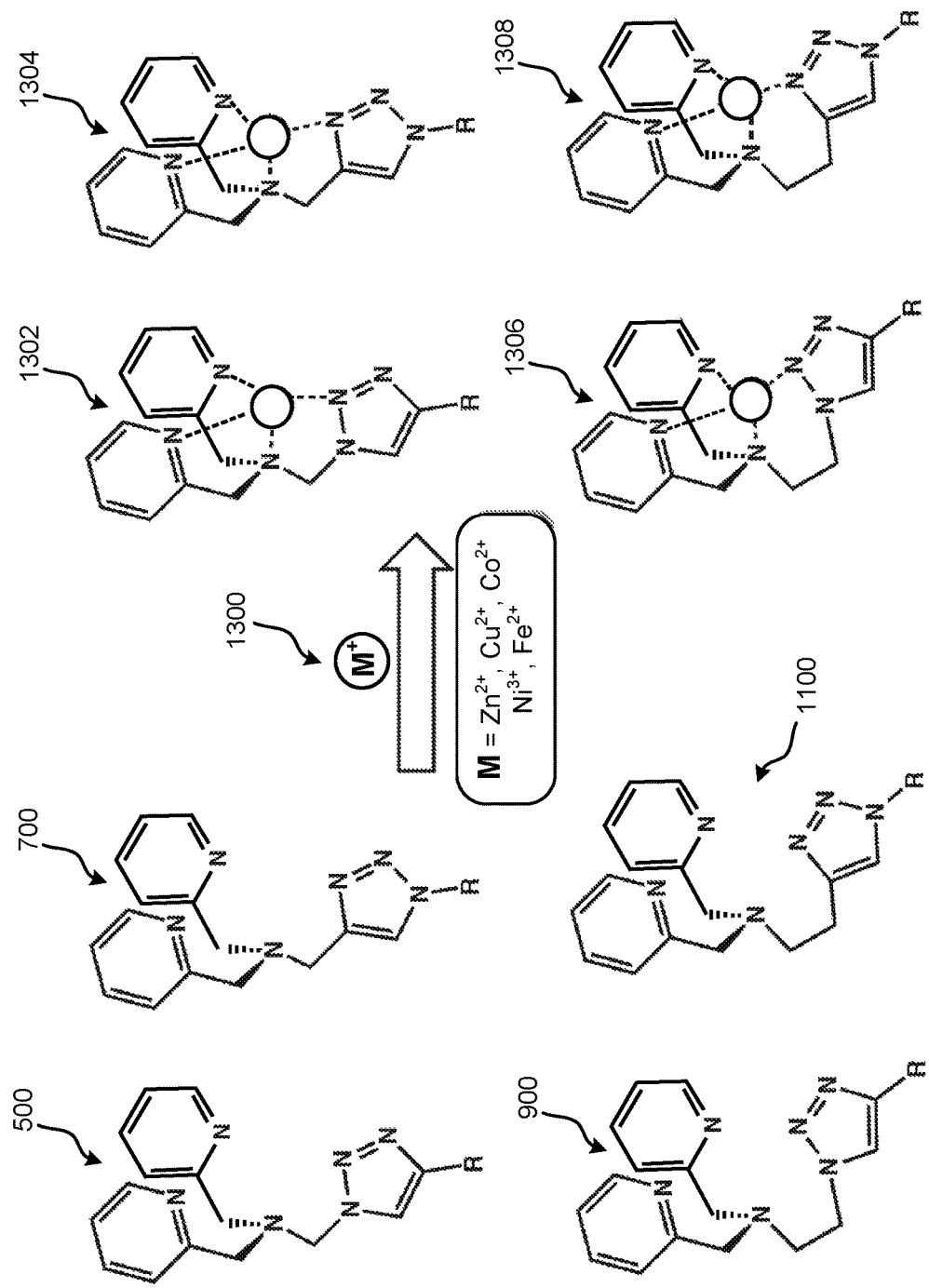
FIG. 13 depicts a simplified reaction scheme for complexing bis(2-pyridylmethyl)amine-based ligands with a metal cation to form the novel catalysts disclosed herein, according to one embodiment.

It is also of note that following synthesis, the bis(2-pyridylmethyl)amine-based ligands 500, 700, 900 and 1100 described in FIGS. 5, 7, 9, and 11, respectively, may each be preferably complexed with a metal cation 1300 (e.g., $M^{2+}$/$M^{3+}$) as shown in FIG. 13, according to some approaches. Complexation of the bis(2-pyridylmethyl)amine-based ligands 500, 700, 900, 1100 with the metal cation 1300 produces the catalytic bis(2-pyridylmethyl)amine-based ligand-metal complexes 1302, 1304, 1306, and 1308, respectively. In various approaches, the bis(2-pyridylmethyl)amine-based ligands 500, 700, 900 and 1100 may be complexed with different metal ions depending on their intended application, e.g., the degradation of organophosphorus-based compounds, carbon capture applications, the study of triazole-based ligand-metal interactions, etc.

In various approaches, the above complexation may include mixing the bis(2-pyridylmethyl)amine-based ligand and a metal salt in equimolar amounts in an appropriate solvent, such as methanol. Notably, after complexation, the ligand-metal complex may be removed from solution, and subsequently exhibit catalytic activity without relying on organic solvents such as alcohols, caustic agents such as bleach, sodium hydroxide, potassium hydroxide, etc., or other environmentally unfriendly materials as would be understood by a person having ordinary skill in the art upon reading the present descriptions. Rather, the presently disclosed ligand-metal complexes may utilize hydrolytic substitution of a hydroxyl moiety (which may be obtained from a water molecule) for the leaving group of the organophosphorus-based compound, and therefore may carry out catalysis using only environmentally friendly materials such as water to facilitate the catalysis. In various embodiments, humidity of the atmosphere may be sufficient to facilitate the ligand-metal complex mediated catalysis.

As discussed previously, the novel catalysts disclosed herein, such as those including a bis(2-pyridylmethyl) amine-based ligand and a metal cation coordinated thereto, are expected to provide superior catalytic activity for the neutralization of toxicity in organophosphorus-based compounds, at least in part due to the open nature of the structure, which facilitates binding of the metal cation and subsequent catalysis of substitution reactions with organophosphorus-based compounds. In particular, for the bis(2-pyridylmethyl)amine-based ligand-metal complexes disclosed herein, the increased acidity facilitates catalysis of organophosphorus-based compounds. For instance, reacting the presently disclosed bis(2-pyridylmethyl)amine-based ligand-metal complexes with an organophosphorus-based compound effectively neutralizes the toxicity of the organophosphorus-based compound by substituting a hydroxyl moiety for the leaving group of the organophosphorus-based compound. Thus, in preferred approaches the presently disclosed bis(2-pyridylmethyl)amine-based ligand-metal complexes, when conjugated with a water molecule, preferably exhibit a $pK_a$ with respect to the water molecule in a range from about 6.0 to about 10.0, more preferably from about 6.5 to about 8.1. As utilized herein, the term "about" should be understood to encompass ±10% of the stated value(s).

Figure 14A:
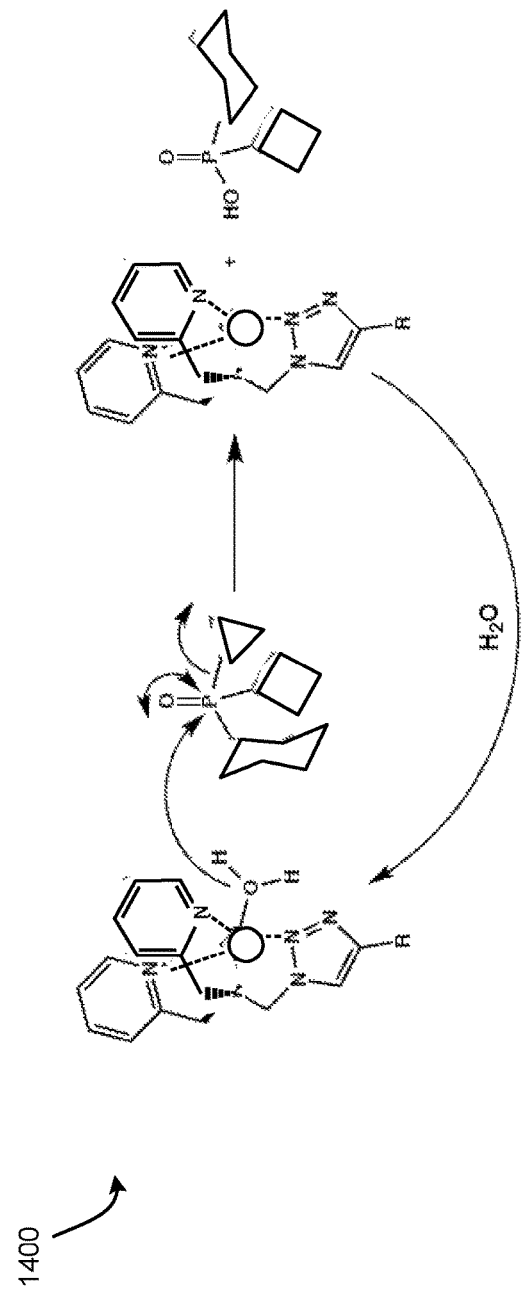
FIGS. 14A-14B depict exemplary reaction schemes by which the novel catalysts disclosed herein (e.g., bis(2-pyridylmethyl)amine-based ligand-metal complexes) may catalyze organophosphorus-based compounds and effectively neutralize the toxicity thereof, according to various embodiments.
Figure 14B:
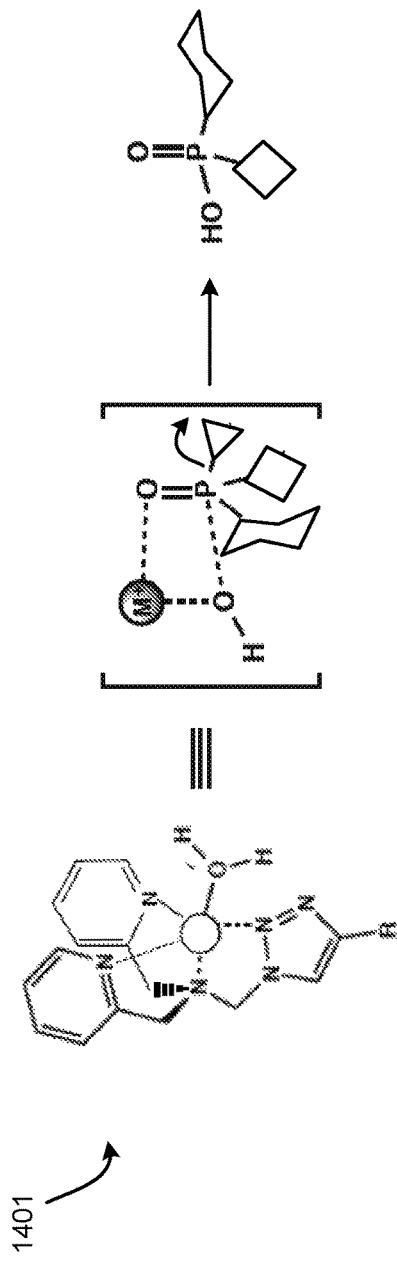

FIGS. 14-14B provides exemplary reaction schemes 1400, 1401 for the degradation of organophosphorus-based compounds utilizing an illustrative bis(2-pyridylmethyl) amine-based ligand-metal complex, according to one embodiment. The exemplary reaction schemes 1400, 1401 may be implemented in conjunction with features from any other embodiment listed herein, such as those described with reference to the other FIGS. Of course, the exemplary reaction schemes 1400, 1401 and others presented herein may be used in various applications and/or in permutations, which may or may not be specifically described in the illustrative embodiments listed herein. Moreover, more or less operations than those shown in FIG. 14 may be included in the exemplary reaction schemes 1400, 1401, according to various embodiments.

Figure 1E:
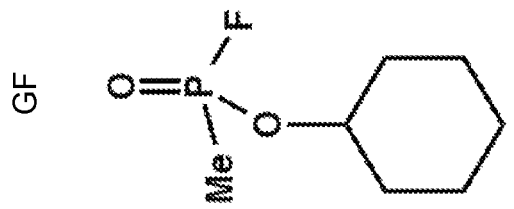
FIGS. 1A-1E depict simplified schematics of exemplary organophosphorus-based compounds suitable for degradation catalyzed by the presently disclosed inventive bis(2-pyridylmethyl)amine-based compounds, according to various embodiments.
Figure 1D:
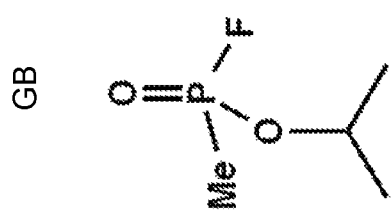
Figure 1C:
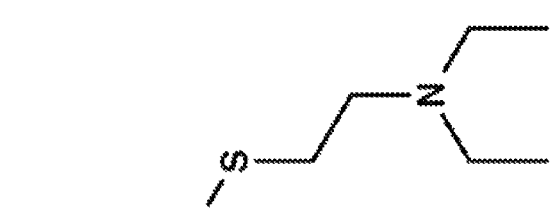
Figure 1B:
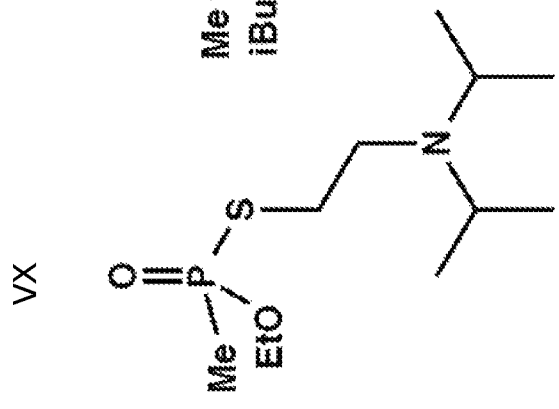
Figure 1A:
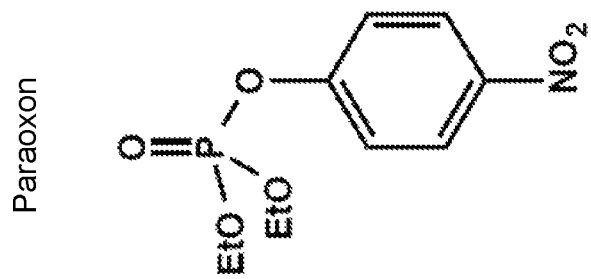

As shown in FIGS. 14A-14B, there are two proposed pathways 1400, 1401 for the function of the presently disclosed bis(2-pyridylmethyl)amine-based ligand-metal complexes. Reaction scheme 1400 shown in FIG. 14A involves a bimolecular reaction with the direct transfer of the hydroxide ion to the P-center of the organophosphorus-based compound, with concomitant expulsion of the organophosphorus-based compound's best leaving group. Thus, in the case of Paraoxon (FIG. 1A), the leaving group is expected to be the nitrophenolate ion ($pK_a$ of conjugate acid=7.1), while for the G-series (FIGS. 1D-1E) and the V-series (FIGS. 1B-1C) agents it is expected to be the fluoride ion ($pK_a$ of conjugate acid=3.2) and the thiolate anion ($pK_a$ of conjugate acid=8.6) respectively.

Reaction scheme 1401, shown in FIG. 14B, involves another bimolecular reaction but with a previous, ordered coordination of the metal center with the oxygen atom of the P=O region of the organophosphorus-based compound. As in the first proposed mechanism, once the coordination has occurred, the hydroxide ion is transferred from the complex to the agent with concomitant departure of the leaving group.

It is expected in these proposed reaction schemes that the organophosphorus-based compound's best leaving group (i.e., the arm with the lowest pKa value) should depart every time said compound encounters the catalyst (e.g., the bis(2-pyridylmethyl)amine-based ligand-metal complex), however this may not always be the case. For instance, other groups in the organophosphorus-based compounds may leave as well, as in the case of Paraoxon, where products were formed from the departure of both the nitrophenolate ion and the unexpected ethoxide ion. Without wishing to be bound to any particular theory, it is thought that there may be an intermediate at play during these reactions, and since the phosphorus-center can accommodate extra substituents to form trigonal bipyramidal structures, it is further postulated that anti-orientation of the entering hydroxide ion and the leaving group may play a small role indeed.

As discussed above, the presently disclosed novel catalysts may be embodied according to any of the above descriptive examples, in various approaches. Additionally, in preferred approaches, the presently disclosed novel catalysts may be embodied as follows.

In one embodiment, a catalyst may include a bis(2-pyridylmethyl)amine-based ligand. The bis(2-pyridylmethyl)amine-based ligand may preferably include at least three $sp^2$ nitrogen atoms and at least one sp3 nitrogen atom positioned within the catalyst in a location suitable to coordinate/complex a metal cation placed in proximity with the bis(2-pyridylmethyl)amine-based ligand.

In various approaches, the bis(2-pyridylmethyl)amine-based ligand of the catalyst may include a bis(2-pyridylmethyl)amine-based scaffold and a heterocyclic amine moiety coupled thereto. The bis(2-pyridylmethyl)amine-based scaffold may include at least two $sp^2$ nitrogen atoms and at least one $sp^3$ nitrogen atom, and the heterocyclic amine moiety may include at least one $sp^2$ nitrogen atom. Additionally, the heterocyclic amine moiety may be selected from the group consisting of: a triazole, an imidazole, a thiazole, an oxazole, and a pyrazole. In particular approaches, the bis(2-pyridylmethyl)amine-based ligand may have the structure as substantially shown in FIGS. 5, 7, 9 and 11, where R groups depicted therein may include one or more of hydrogen, an electron donating group, an electron withdrawing group, an alcohol, and PEG.

In more approaches, the catalyst may preferably include at least one metal cation complexed to the nitrogen atoms of the bis(2-pyridylmethyl)amine-based ligand, where the metal cation may include, but is not limited to, $Cu^{2+}$, $Zn^{2+}$, $Co^{2+}$, $Fe^{2+,}$ $Ni^{3+}$, etc. For instance, the bis(2-pyridylmethyl)amine-based ligand-metal complex may have any of the structures as substantially shown in FIG. 13, according to some approaches. The catalyst may also include a hydroxyl moiety functionalized to the metal cation, in preferred approaches.

In additional embodiments, the presently disclosed inventive concepts include techniques for synthesizing and utilizing the aforementioned bis(2-pyridylmethyl)amine-based ligands. For instance, an exemplary method 1500 of forming bis(2-pyridylmethyl)amine-based ligands is shown in FIG. 15, while an exemplary method 1600 for employing bis(2-pyridylmethyl)amine-based catalysts to neutralize toxicity of organophosphorus-based compounds is shown in FIG. 16.

In various embodiments, the methods 1500 and 1600 may be practiced using any suitable materials disclosed herein, and/or proceed according to any suitable reaction scheme, application technique, etc. each as would be understood by a person having ordinary skill in the art upon reading the instant disclosures. Other equivalent reaction schemes, materials, application techniques, etc. that would be understood by a person having ordinary skill in the art upon reading these disclosures may also be employed without departing from the scope of the inventive concepts presented herein.

Figure 15:
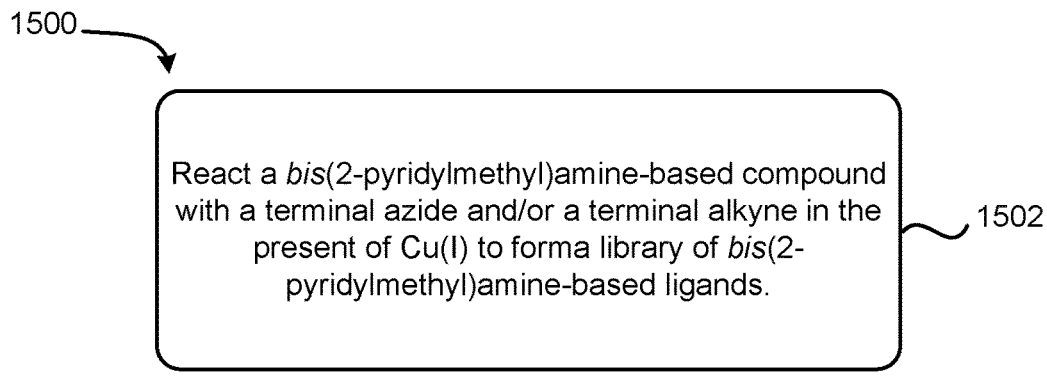
FIG. 15 depicts a flowchart of a method for forming bis(2-pyridylmethyl)amine-based ligands, according to one embodiment.
Figure 16:
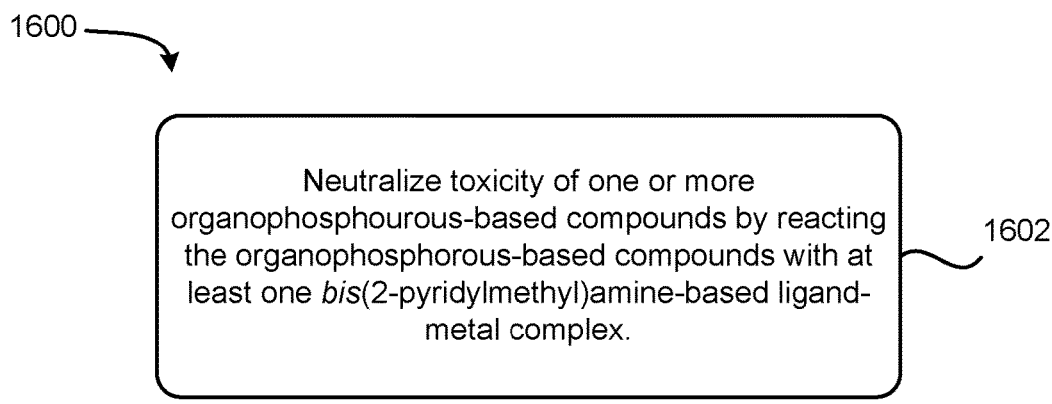
FIG. 16 depicts a flowchart of a method for neutralizing toxicity of organophosphorus-based compounds using the novel catalysts disclosed herein (e.g., bis(2-pyridylmethyl) amine-based ligand-metal complexes), according to one embodiment.

Turning now to FIG. 15, a method 1500 for forming bis(2-pyridylmethyl)amine-based ligands is shown, according to one embodiment. The method 1500 may employ any suitable starting materials, e.g. as shown in FIG. 3, any suitable intermediates, e.g. as shown in FIGS. 6, 8, 10, 12, and result in any suitable final material(s), such as shown in FIGS. 4, 5, 7, 9, 11, in various approaches. Similarly, method 1500 may proceed according to any of the reaction schemes shown in FIGS. 6, 8, 10, 12, among other suitable equivalent schemes as would become apparent to a person having ordinary skill in the art upon reading the present disclosure.

As shown in FIG. 15 the method may include a single step, reflecting the simplicity of the presently disclosed synthetic schemes and techniques. For example, method 1500 includes operation 1502, in which a bis(2-pyridylmethyl)amine-based compound is reacted with a terminal azide and/or a terminal alkyne in the presence of Cu(I) to form a library of bis(2-pyridylmethyl)amine-based ligands. However, the method 1500 may include additional operations, features, etc. without departing from the scope of the present disclosure.

The bis(2-pyridylmethyl)amine-based compound, which reacts with the terminal azide and/or the terminal alkyne, may preferably be one or more of intermediates 602, 804, 1002, and 1202, as shown in FIGS. 6, 8, 10 and 12, respectively; yet, any suitable intermediate that would become apparent to a skilled artisan may be employed without departing from the scope of the present disclosure, in various embodiments.

Preferably, reacting the bis(2-pyridylmethyl)amine-based compound with the terminal azide and/or the terminal alkyne includes Cu(I)-catalyzed azide-alkyne cycloaddition, or "click chemistry." Utilizing click chemistry advantageously increases the efficiency of the synthesis process, as well as generating a variety of bis(2-pyridylmethyl)amine-based ligands with structural variations, permitting investigation into relative advantages of various compounds in various applications.

In further approaches, method 1500 may include complexing the bis(2-pyridylmethyl)amine-based ligands with one or more metal cations. The metal cations may be selected for both catalytic activity and affordability. In various approaches, the metal cation(s) may be selected from a group consisting of: $Cu^{2+}$, $Zn^{2+}$, $Co^{2+}$, $Fe^{2+}$, and $Ni^{3+}$. In more approaches, the metal cation(s) may be complexed with water or a hydroxyl moiety in order to "activate" the catalyst for neutralizing organophosphorus-based compounds. This complexation may be accomplished intentionally by employing particular chemistry, or may occur naturally due to environmental conditions, e.g. sufficient humidity, precipitation, submersion in a body of water, etc. as would become apparent to a person having ordinary skill in the art upon reading the present disclosure.

In yet more approaches, method 1500 may involve functionalizing the bis(2-pyridylmethyl)amine-based ligands, the bis(2-pyridylmethyl)amine-based ligand-metal complexes, the bis(2-pyridylmethyl)amine-based ligand-metal complexes functionalized/complexed to water or a hydroxyl moiety, etc. to a substrate. This substrate may be a surface, a solid support, a planar surface, a three-dimensional surface, nanoparticles, polymers, solid or porous beads (e.g. polymer-based beads, magnetic beads, glass beads, etc.), a resin, a filter, fibers, a matrix, an aerogel, etc. as would become apparent to a person having ordinary skill in the art upon reading the present disclosure. Particularly preferred surfaces/supports may include filters, beads, magnetic nanoparticles, and polymeric fibers. Accordingly, these units may be attached or otherwise functionalized to different places on the substrate, e.g. in order to be used as part of solid network instead of freely floating in a solution.

Turning now to FIG. 16, a method 1600 for neutralizing toxic agents such as organophosphorus-based nerve agents, pesticides, etc. is shown, according to one embodiment. As shown in FIG. 16, the neutralization technique involves operation 1602, which includes reacting at least one bis(2-pyridylmethyl)amine-based ligand-metal complex (such as those disclosed herein) with toxic agents such as organophosphorus-based compounds.

In preferred approaches, the bis(2-pyridylmethyl)amine-based ligand-metal complex may act as catalysts to facilitate substitution of a leaving group of the organophosphorus-based compound with a hydroxyl moiety, preferably a hydroxyl moiety conjugated to the metal cation of the bis(2-pyridylmethyl)amine-based ligand-metal complex.

In various approaches, method 1600 may, of course, include additional features and/or operations as disclosed herein, and as would become apparent to a person having ordinary skill in the art upon reading the present disclosure. For instance, in some approaches, method 1600 may include washing a surface or support to which the bis(2-pyridylmethyl)amine-based ligand-metal complex is functionalized, e.g. to carry away neutralized agent, re-activate the bis(2-pyridylmethyl)amine-based ligand-metal complex for subsequent neutralization, etc.

In additional approaches, the reaction may benefit from agitation, stirring, etc., e.g. where the sample to be treated includes a liquid sample or a solid sample submerged in a solution of bis(2-pyridylmethyl)amine-based ligand-metal complex and a suitable solvent/buffer composition. Similarly, where the sample to be treated includes a surface, and particularly a large surface, the reaction may benefit from applying an excess of the bis(2-pyridylmethyl)amine-based ligand-metal complex via spraying a solution thereof over the surface.

In yet more approaches where the bis(2-pyridylmethyl)amine-based ligand-metal complex may be functionalized to magnetic beads and where retrieval of said catalysts is desirable, method 1600 may include applying a magnetic field to the treated sample, solution, environment, etc. to facilitate recovery of the bis(2-pyridylmethyl)amine-based ligand-metal complex. Retrieval may optionally include a step of drying, concentrating (e.g. via centrifugation), washing, etc. the beads and functionalized bis(2-pyridylmethyl)amine-based ligand-metal complex, as well as eluting the bis(2-pyridylmethyl)amine-based ligand-metal complex from the beads using an appropriate solvent. The eluted bis(2-pyridylmethyl)amine-based ligand-metal complex may be subsequently functionalized to magnetic nanoparticles, or other surfaces, supports, etc. for re-use or use in a different capacity, e.g., in a filter.

APPLICATIONS

The presently disclosed inventive concepts, materials, etc. may be advantageously employed in a broad range of applications, forms, and techniques to accomplish neutralization of organophosphorus-based compounds. The capability to present these materials and techniques in a wide variety of forms, e.g., as liquid, functionalized on solid surfaces, functionalized on particulates (especially nanoparticles), as an aerosol, etc. advantageously allow the effective neutralization techniques to be implemented in a wide variety of scenarios in which the toxic organophosphorus-based compounds may be encountered in practice.

For instance, in one approach a body of water may become contaminated with organophosphorus-based compounds, in which case the presently disclosed inventive materials and techniques may be utilized to treat the water, e.g., with either the catalyst itself in its free form, or as mixture in the water, e.g., to disinfect using compounds beyond the scope of the present disclosure, as well as decontaminate the water from organophosphorus-based compounds using compounds as disclosed herein.

In particular approaches, the novel catalysts disclosed herein (e.g., the bis(2-pyridylmethyl)amine-based ligand-metal complexes) may be functionalized to a metal surface like magnetic beads for example, and subsequently added to a contaminated solution, body of water, etc. such that the magnetic beads can perform the destruction of the agent present in the water. Upon completion of decontamination, it is possible to retrieve the magnetic beads, and thus the bound catalysts, using a magnet. This approach advantageously avoids contaminating the treated sample, surface, solution, etc. with the bis(2-pyridylmethyl)amine-based catalysts, which may be useful if the bis(2-pyridylmethyl) amine-based catalysts themselves are undesirable for the intended purpose/use of the sample, surface, solution, etc.

Similarly, in various approaches other substrate materials may be employed, such as glass beads, polymer fibers, matrices, etc. as would become apparent to a person having ordinary skill in the art upon reading the present disclosure.

In more approaches, particular metals such as gold for example may be employed as a substrate material. For instance, gold may be particularly advantageous as a substrate material where a thiol group may be cleaved from the organophosphorus-based compound (or otherwise generated in the course of neutralization). Since thiol groups have a strong affinity for gold, using gold as the substrate material may encourage free thiols to bind/complex with the gold rather than attempting to complex with the metal cation catalyzing the substitution reaction. In this manner, inhibitory effects caused by products of the intended catalysis may be mitigated or avoided, in various approaches.

Similarly, from an academic perspective gold or other suitable metals may be useful in the context of enabling investigation of the inventive bis(2-pyridylmethyl)amine-based ligands, and their activity, e.g. via Raman spectroscopy.

In yet more approaches, the presently disclosed inventive bis(2-pyridylmethyl)amine-based catalysts may be functionalized on armor panels to provide protection against chemical agent deployment to military personnel, law enforcement, emergency service personnel, etc. as would be understood by a person having ordinary skill in the art upon reading the present disclosures.

Accordingly, the presently disclosed inventive bis(2-pyridylmethyl)amine-based catalysts may be embodied as a spray solution, an aerosol, etc. to facilitate rapid and facile application to contaminated surfaces, samples, etc.

In further approaches, the presently disclosed inventive bis(2-pyridylmethyl)amine-based catalysts may be embedded it into filters.

In additional approaches, the presently disclosed inventive bis(2-pyridylmethyl)amine-based catalysts may be utilized in carbon capture processes (e.g., to catalyze the conversion of $CO_2$ into carbonate). For example, in one embodiment, a method for capturing $CO_2$ may include contacting the bis(2-pyridylmethyl)amine-based catalysts disclosed herein with a gas comprising $CO_2$ to at least partially remove $CO_2$ from the gas. In some approaches, such a method may include contacting a solution, e.g. an aqueous solution, comprising a bis(2-pyridylmethyl)amine-based catalyst to a gas comprising $CO_2$ in order to at least partially remove $CO_2$ from the gas. In other approaches, this method may include contacting a capsule, bead, porous receptacle, etc. to which the bis(2-pyridylmethyl)amine-based catalysts is coupled/associated to a gas comprising $CO_2$ in order to at least partially remove $CO_2$ from the gas. In preferred approaches, there may be no liberation of $CO_2$ after the reaction has taken place. In the case of CO2 hydration, the catalyst would carry out the conversion $CO_2$ into bicarbonate, a process that is very different from the conventionally-used amine-based methods that in fact trap CO2 and can liberate it back via heating.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A catalyst, comprising:
   a ligand comprising a bis(2-pyridylmethyl)amine group, wherein the ligand comprises at least three $sp^2$ nitrogen atoms and at least one sp3 nitrogen atom, and wherein the ligand has a structure selected from the group consisting of:

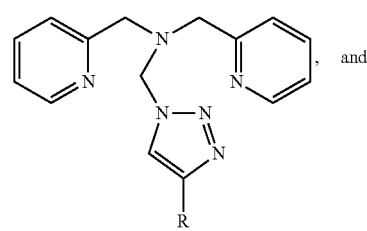

-continued

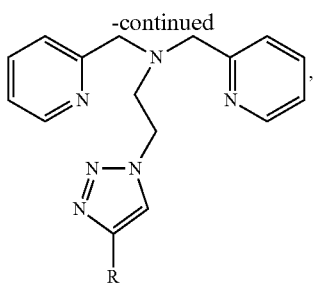

wherein each R is independently selected from the group consisting of: hydrogen, an ester, an alcohol, and polyethylene glycol (PEG); and at least one metal cation complexed to the nitrogen atoms of the ligand, wherein the at least one metal cation includes one or more of: $Zn^{2+}$, and $Co^{2+}$.

2. The catalyst as recited in claim 1, wherein the metal cation is $Co^{2+}$.

3. The catalyst as recited in claim 1, wherein the metal cation is $Zn^{2+}$.

4. The catalyst as recited in claim 1, comprising a hydroxyl group functionalized to the metal cation.

5. The catalyst as recited in claim 1, wherein the ligand has the structure

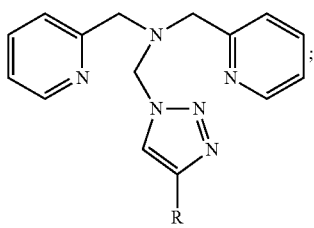

and wherein R is hydrogen.

6. The catalyst as recited in claim 1, wherein the ligand has the structure

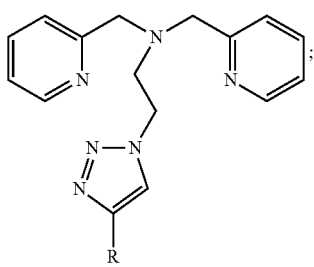

and wherein R is hydrogen.

7. The catalyst as recited in claim 1, wherein R is hydrogen.

8. A catalyst, comprising a ligand, wherein the ligand has a structure selected from the group consisting of:

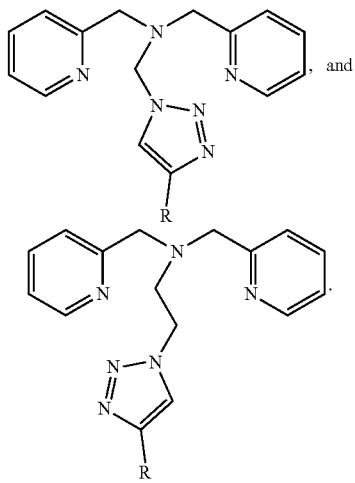, and wherein each R is independently selected from the group consisting of: hydrogen, an ester, an alcohol, and polyethylene glycol (PEG).

9. The catalyst as recited in claim 8, wherein R is hydrogen.

10. The catalyst as recited in claim 8, wherein the ligand has the structure

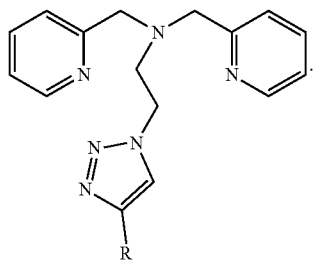

11. The catalyst as recited in claim 8, wherein the ligand has the structure

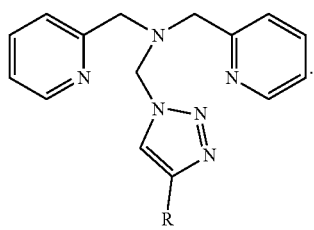

12. The catalyst as recited in claim 8, comprising at least one metal cation complexed to the ligand.

13. The catalyst as recited in claim 12, wherein the at least one metal cation is selected from the group consisting of: $Cu^{2+}$, $Zn^{2+}$, $Co^{2+}$, and $Fe^{2+}$.

14. A method of forming a catalyst as recited in claim 1, the method comprising:

reacting bis(2-pyridylmethyl)amine-based compound with a terminal azide or a terminal alkyne in the presence of Cu(I) to form the bis(2-pyridylmethyl)amine-based ligand.

* * * * *